United States Patent
Takagi et al.

(10) Patent No.: US 11,980,455 B2
(45) Date of Patent: May 14, 2024

(54) MEASURING DEVICE

(71) Applicant: Murata Manufacturing Co., Ltd., Nagaokakyo (JP)

(72) Inventors: Jun Takagi, Nagaokakyo (JP); Kenji Tanaka, Nagaokakyo (JP); Tomoki Takahashi, Nagaokakyo (JP)

(73) Assignee: MURATA MANUFACTURING CO., LTD., Nagaokakyo (JP)

( * ) Notice: Subject to any disclaimer, the term of this patent is extended or adjusted under 35 U.S.C. 154(b) by 229 days.

(21) Appl. No.: 17/538,179

(22) Filed: Nov. 30, 2021

(65) Prior Publication Data

US 2022/0087567 A1 Mar. 24, 2022

Related U.S. Application Data

(63) Continuation of application No. PCT/JP2020/021677, filed on Jun. 2, 2020.

(30) Foreign Application Priority Data

Jun. 7, 2019 (JP) .................................. 2019-106731

(51) Int. Cl.
*A61B 5/0537* (2021.01)
*A61B 5/00* (2006.01)
(Continued)

(52) U.S. Cl.
CPC ............ *A61B 5/0537* (2013.01); *A61B 5/682* (2013.01); *G01N 27/223* (2013.01); *A61B 2562/0209* (2013.01)

(58) Field of Classification Search
CPC ........ A61B 5/00; A61B 5/0537; G01N 27/22; G01N 19/10; H01L 29/41
See application file for complete search history.

(56) References Cited

U.S. PATENT DOCUMENTS

| | | | | |
|---|---|---|---|---|
| 2001/0006256 A1* | 7/2001 | Nakashima | ......... | H01L 23/4824 257/758 |
| 2002/0109959 A1 | 8/2002 | Toyoda et al. | | |
| 2006/0203319 A1* | 9/2006 | Kouma | ............... | B81C 1/00547 359/224.1 |

FOREIGN PATENT DOCUMENTS

| | | | |
|---|---|---|---|
| JP | 2001021517 A | | 1/2001 |
| JP | 2001189420 A | | 7/2001 |
| | (Continued) | | |

OTHER PUBLICATIONS

International Search Report issued in PCT/JP2020/021677, dated Jul. 21, 2020.

(Continued)

*Primary Examiner* — Neel D Shah
(74) *Attorney, Agent, or Firm* — Arentfox Schiff LLP

(57) ABSTRACT

A measuring device is provided for reducing the occurrence of damage to a sensor section. The sensor section includes a substrate, a pair of comb electrodes on a first principal surface, and a pair of back-side electrodes disposed on a second principal surface and corresponding to the pair of comb electrodes, respectively. The pair of comb electrodes includes a plurality of tooth sections and connection sections that connect the tooth sections to each other, respectively. The substrate includes via-hole conductors in positions corresponding to the tooth sections inside a region surrounded by the outer tooth sections on opposite ends in a direction in which the tooth sections in the pair of comb electrodes are aligned and the connection sections. The via-hole conductors connect the comb electrodes and the back-side electrodes.

18 Claims, 15 Drawing Sheets

(51) Int. Cl.
    *G01N 27/22*     (2006.01)
    *G01R 19/10*     (2006.01)

(56) References Cited

FOREIGN PATENT DOCUMENTS

| | | |
|---|---|---|
| JP | 2002243689 A | 8/2002 |
| JP | 2005114357 A | 4/2005 |
| JP | 2005287547 A | 10/2005 |
| JP | 2006286772 A | 10/2006 |
| JP | 2009089869 A | 4/2009 |
| JP | 2013195118 A | 9/2013 |
| WO | 2004028359 A1 | 4/2004 |

OTHER PUBLICATIONS

Written Opinion of the International Searching Authority issued in PCT/JP2020/021677, dated Jul. 21, 2020.

\* cited by examiner

MEASURING DEVICE

CROSS REFERENCE TO RELATED APPLICATIONS

The present application is a continuation of PCT/JP2020/021677 filed Jun. 2, 2020, which claims priority to Japanese Patent Application No. 2019-106731, filed Jun. 7, 2019, the entire contents of each of which are incorporated herein by reference.

TECHNICAL FIELD

The present invention relates to a measuring device.

BACKGROUND

Patent Documents 1 and 2 (identified below) provide examples of measuring devices for measuring an object held by a hand of a measurer, and, more particularly, are examples of oral cavity moisture measuring devices. Such measuring devices include a capacitive sensor section at a leading end of a probe section that measures the moisture content of the object while a measurement surface of the sensor section is pressed to a surface to be measured of a tongue mucous membrane or the like, as the object.

In one example, the sensor section in the measuring device in Patent Document 2 includes comb electrodes having the shape of a toothed comb and disposed on a first principal surface of a substrate and an amplifier circuit disposed on a second principal surface of the substrate. In the sensor section, the comb electrodes and the amplifier circuit are electrically connected to each other with a conductive member interposed therebetween, and with the conductive member disposed inside a via hole (contact hole) in the substrate.

Patent Document 1: International Publication No. 2004/028359.
Patent Document 2: Japanese Unexamined Patent Application Publication No. 2005-287547.

The above-described sensor section used in the measuring device includes the pair of comb electrodes on the principal surface of the substrate, and when the measurement surface of the sensor section is pressed to the surface to be measured to perform measurement, an external force (e.g., a load) occurring with the pressing acts on the sensor section. That operation and force may cause damage to the sensor section.

SUMMARY OF THE INVENTION

Accordingly, it is an object of the exemplary embodiments of the present invention to provide a measuring device constructed with reduced occurrence of damage to a sensor section.

In one exemplary aspect, a measuring device is provided that includes a sensor section including a substrate having a first principal surface and a second principal surface, a pair of comb electrodes disposed on the first principal surface, and a pair of back-side electrodes disposed on the second principal surface and corresponding to the pair of the comb electrodes, respectively. Each of the pair of comb electrodes includes a plurality of tooth sections and a connection section connecting the tooth sections. The substrate includes via-hole conductors in positions corresponding to the tooth sections inside a region surrounded by the tooth sections on opposite ends in a direction in which the plurality of tooth sections in the pair of comb electrodes are aligned and the connection sections in the pair of comb electrodes. The via-hole conductors connect the comb electrodes and the back-side electrodes.

According to the configuration of the exemplary embodiment, because the via-hole conductors, where many interfaces of different kinds are present and the effect of deformation caused by the external force tends to concentrate on, are arranged in position corresponding to the tooth sections inside the region surrounded by the tooth sections on the opposite ends in the direction in which the plurality of tooth sections in the pair of comb electrodes are aligned and the connection sections in the pair of comb electrodes, the via-hole conductors are surrounded by the tooth sections and the connection sections. Thus, in comparison with the case where the positions of the via-hole conductors are set at the connection sections or the case where the they are set at the tooth sections on the opposite ends in the direction in which the plurality of tooth sections in the comb electrodes are aligned, the external force is more smoothly dispersed, and thus the external force acting on the comb electrodes can be released from the via-hole conductors. In particular, the technical advantage of resisting the external force is improved by placing the via-hole conductors in a relatively inner area (e.g., a central area), and thus damage to the sensor section is reduced.

The measuring device according to the exemplary embodiment of the present invention reduces the occurrence of damage to the sensor section.

DETAILED DESCRIPTION OF EMBODIMENTS

Exemplary embodiments are described below with reference to the accompanying drawings.

In the accompanying drawings, the illustrations of components may be enlarged for facilitating the understanding. The dimensional ratios of the components may differ from real ones or ones in a different drawing.

First Exemplary Embodiment

Figure 1:
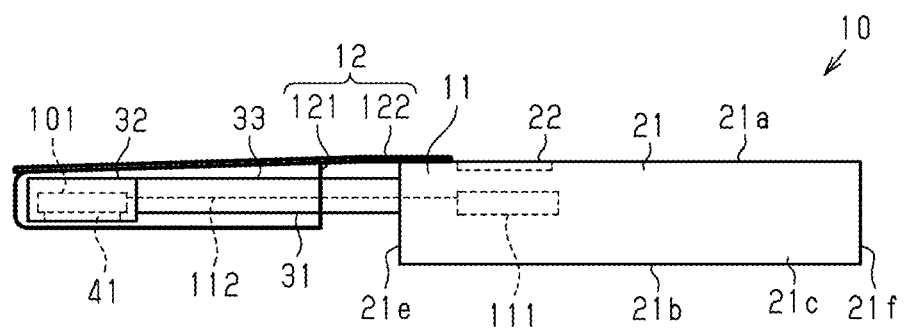
FIG. 1 is a schematic side view of a measuring device according to a first exemplary embodiment.

As illustrated in FIG. 1, a measuring device 10 includes a main body 11 and a cover 12 attached to the main body 11. Moreover, the measuring device 10 can be an oral cavity moisture measuring device for measuring the moisture content in an oral cavity as an example of a target for measurement.

Figure 2:
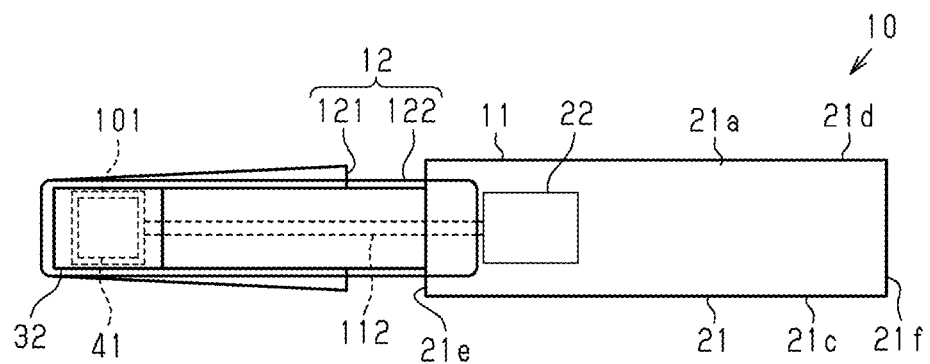
FIG. 2 is a schematic plan view of the measuring device according to the first exemplary embodiment.

As illustrated in FIGS. 1 and 2, the main body 11 includes a grip section 21 being a first end portion region (also referred to as a "first end") of the main body 11 in the longitudinal direction and a probe section 31 being a second end portion region (also referred to as a "second end") of the main body 11 in the longitudinal direction.

As shown, the grip section 21 (also referred to as a "grip") has a substantially cuboid shape that is longer in the same direction as the longitudinal direction of the main body 11 and includes an upper surface 21a, a lower surface 21b, side surfaces 21c and 21d, and end surfaces 21e and 21f. In an exemplary aspect, a display section 22 (also referred to as a "display") for displaying results of measurement and the like is disposed in the upper surface 21a of the grip section 21.

The probe section 31 (also referred to as a "probe") protrudes from the first end surface 21e of the grip section 21. In the present embodiment, the probe section 31 includes a head section 32 (also referred to as a "head") and an arm section 33 (also referred to as an "arm") connecting the head section 32 to the grip section 21.

Moreover, the head section 32 has a cuboid plate shape. The head section 32 includes a sensor section 41 (also referred to as a "sensor") and an oscillation circuit section 101 (also referred to as an "oscillation circuit").

Figure 3:
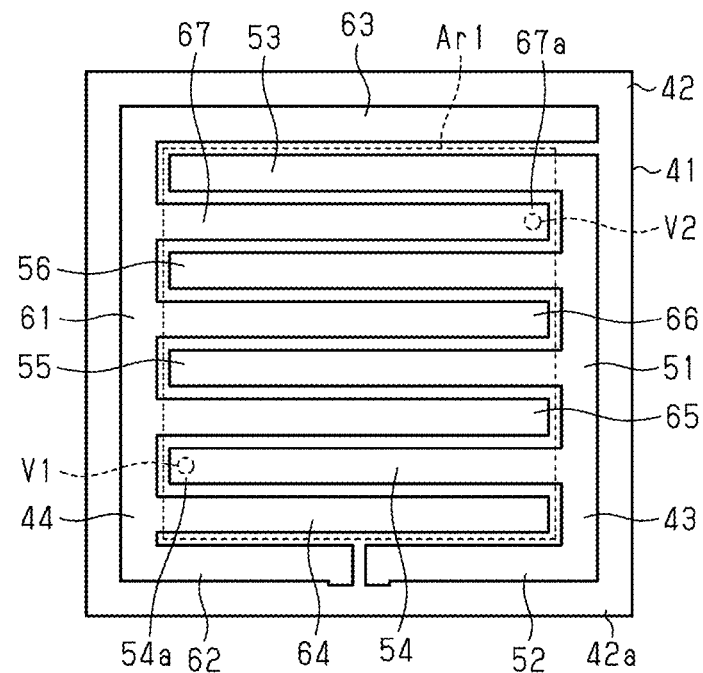
FIG. 3 is a schematic plan view of a sensor section according to the first exemplary embodiment.
Figure 4:
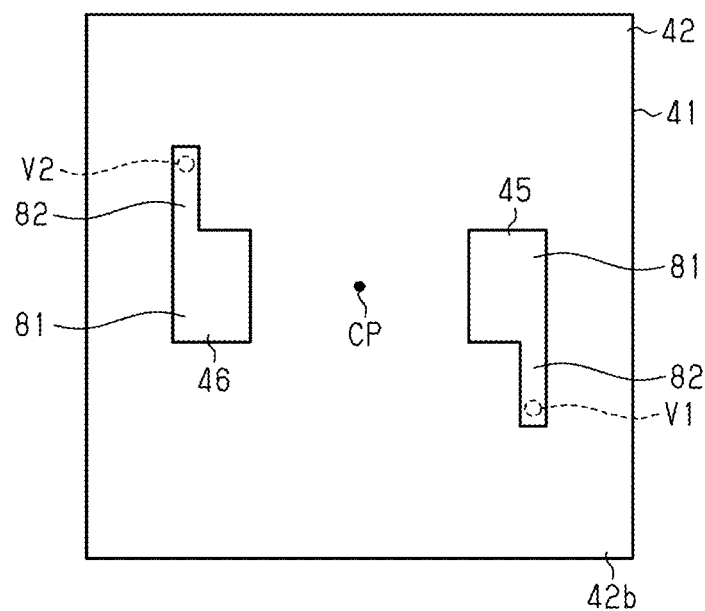
FIG. 4 is a schematic bottom view of the sensor section according to the first exemplary embodiment.
Figure 5:
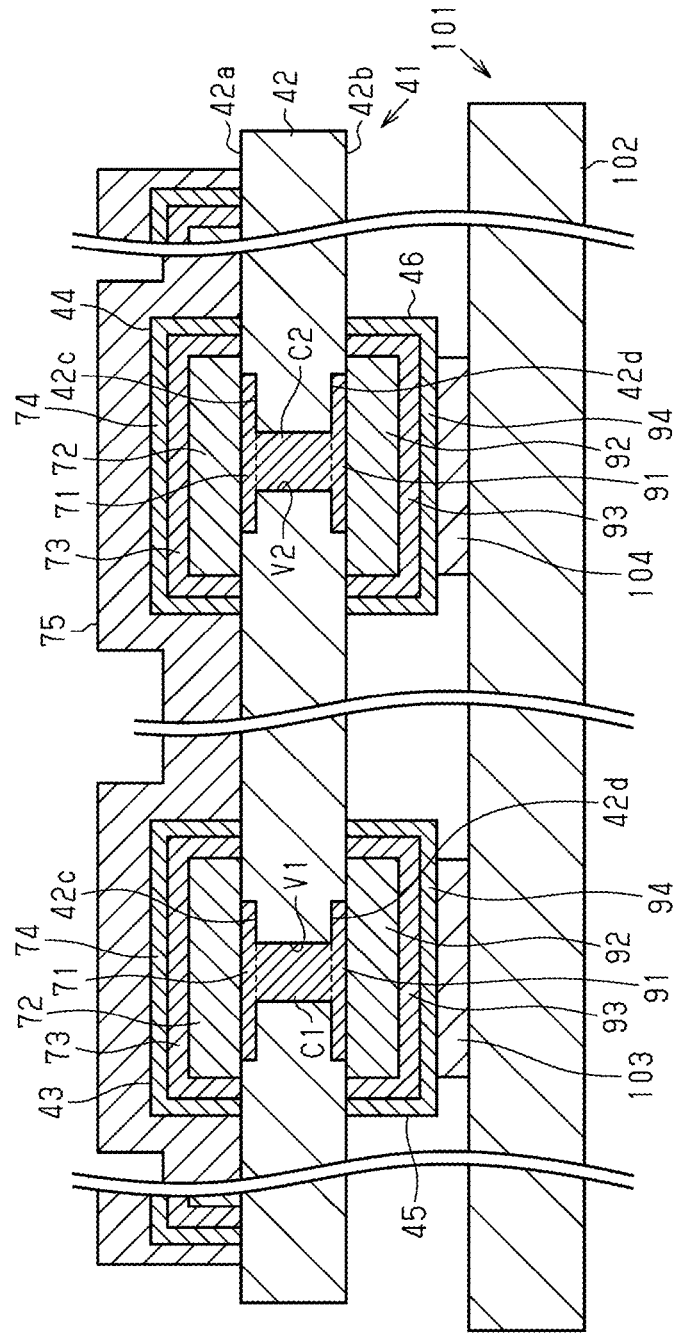
FIG. 5 is a cross-sectional view of the sensor section according to the first exemplary embodiment.

As illustrated in FIGS. 3 to 5, the sensor section 41 includes a substrate 42 having a substantially rectangular plate shape and including a first principal surface 42a and a second principal surface 42b, comb electrodes 43 and 44 disposed on the first principal surface 42a of the substrate 42, and back-side electrodes 45 and 46 disposed on the second principal surface 42b of the substrate 42. In the present embodiment, the two comb electrodes 43 and 44 and the two back-side electrodes 45 and 45 are disposed on the substrate 42 in the sensor section 41. That is, the sensor section 41 includes the pair of comb electrodes 43 and 44 and the pair of back-side electrodes 45 and 46. Moreover, each of the comb electrodes 43 and 44 and the back-side electrodes 45 and 46 is made of a conductive material.

As illustrated in FIG. 3, the comb electrode 43, which is one of the pair of comb electrodes 43 and 44, has the shape of a toothed comb and includes a connection section 51 and a plurality of tooth sections 52 to 56.

The connection section 51 in the comb electrode 43 is elongated in one direction. In one exemplary aspect of the connection section 51, the comb electrode 43 can extend in the direction in which the tooth sections 52 to 56 are aligned. In one exemplary aspect, the longitudinal direction of the connection section 51 can be substantially the same as the longitudinal direction of the main body 11.

The plurality of tooth sections 52 to 56 in the comb electrode 43 extends from the connection section 51 in a direction perpendicular to the longitudinal direction of the connection section 51. In other words, the tooth sections 52 to 56 are connected together by the connection section 51. The tooth sections 52 to 56 are spaced in the longitudinal direction of the connection section 51. In the present embodiment, the five tooth sections 52 to 56 are disposed.

The comb electrode 44, which is the other one of the pair of comb electrodes 43 and 44, has the shape of a toothed comb and includes a connection section 61 and a plurality of tooth sections 62 to 67.

The connection section 61 in the comb electrode 44 is elongated in one direction. In one exemplary aspect of the connection section 61, the comb electrode 44 can extend in the direction in which the tooth sections 62 to 67 are aligned. The connection section 61 is elongated in the same direction as that of the connection section 51 in the comb electrode 43. That is, the longitudinal direction of the connection section 61 can be substantially the same as the longitudinal direction of the main body 11.

The plurality of tooth sections 62 to 67 in the comb electrode 44 extends from the connection section 61 in a direction perpendicular to the longitudinal direction of the connection section 61. In other words, the tooth sections 62 to 67 are connected together by the connection section 51. The tooth sections 62 to 67 are spaced in the longitudinal direction of the connection section 61. In the present embodiment, the six tooth sections 62 to 67 are disposed. That is, the number of the tooth sections 52 to 56 in the comb electrode 43 and the number of the tooth sections 62 to 67 in the comb electrode 44 are different in the exemplary aspect.

In the description below, among the tooth sections 52 to 56 in the comb electrode 43, the tooth sections on the opposite ends in the longitudinal direction of the connection section 51, that is, in the direction in which the tooth sections 52 to 56 are aligned are referred to as the outer tooth sections 52 and 53 in the comb electrode 43, and the tooth sections arranged between the two outer tooth sections 52 and 53 in the direction in which the tooth sections 52 to 56 are aligned are referred to as the inner tooth sections 54 to 56 in the comb electrode 43. Similarly, among the tooth sections 62 to 67 in the comb electrode 44, the tooth sections on the opposite ends in the longitudinal direction of the connection section 61, that is, in the direction in which the tooth sections 62 to 67 are aligned are referred to as the outer tooth sections 62 and 63 in the comb electrode 44, and the tooth sections arranged between the two outer tooth sections 62 and 63 in the direction in which the tooth sections 62 to 67 are aligned are referred to as the inner tooth sections 64 to 67 in the comb electrode 44. The comb electrodes 43 and 44 are arranged such that the tooth sections 52 to 56 in the comb electrode 43 and the tooth sections 62 to 67 in the comb electrode 44 are spaced at predetermined intervals from one another.

Among the tooth sections 52 to 56 and 62 to 67 in the pair of comb electrodes 43 and 44 described above, of the outer tooth sections 52, 53, 62, and 63, the outer tooth section 52 in the comb electrode 43 and the outer tooth section 62 in the comb electrode 44 are opposite to each other in the direction in which the tooth sections extend.

The distance between the tail end of the outer tooth section 52 and the tail end of the outer tooth section 62 (also referred to as the "tail end gap") may be, but not limited to, the same or substantially the same as each of the predetermined intervals described above. Of the tooth sections 52 to 56 and 62 to 67 in the pair of comb electrodes 43 and 44, in sequence from the outer tooth section 52 and the outer tooth section 62, the inner tooth section 64, the inner tooth section 54, the inner tooth section 65, the inner tooth section 55, the inner tooth section 66, the inner tooth section 56, the inner tooth section 67, the outer tooth section 53, and the outer tooth section 63 are aligned. That is, the inner tooth sections 54 to 56 and 64 to 67 and the outer tooth section 53 are disposed between the outer tooth sections 52 and 62 and the outer tooth section 63.

As illustrated in FIG. 5, each of the comb electrodes 43 and 44 is a laminate of a plurality of metal layers 71, 72, 73, and 74. That is, each of the connection sections 51 and 61 and the tooth sections 52 to 56 and 62 to 67 in the comb electrodes 43 and 44 is the laminate of the plurality of metal layers 71, 72, 73, and 74.

Among the plurality of metal layers 71, 72, 73, and 74, the first metal layer 71, which is the lowest layer (nearer the substrate 42), is disposed substantially entirely along a groove section 42c of the substrate 42. In an exemplary aspect, the groove section 42c can conform to the shape of each of the comb electrodes 43 and 44. One example of the first metal layer 71 may be made of silver (Ag). The second metal layer 72 is disposed so as to cover all of the first metal layer 71. One example of the second metal layer 72 may be a nickel (Ni) film and have a thickness of about 5.0 µm. The third metal layer 73 is disposed so as to cover all of the second metal layer 72. One example of the third metal layer 73 may be a palladium (Pd) film and have a thickness of about 0.15 µm. The fourth metal layer 74 is disposed so as to cover all of the third metal layer 73. One example of the fourth metal layer 74 may be a gold (Au) film and have a thickness of about 0.07 µm. It is noted that the thickness and material of each of the first metal layer 71, second metal layer 72, third metal layer 73, and fourth metal layer 74 are provided as exemplary aspects and can be changed as appropriate.

As illustrated in FIG. 4, each of the pair of the back-side electrodes 45 and 46 includes a base section 81 and an extending section 82. The base section 81 has a rectangular shape. The extending section 82 extends from the base section 81. The back-side electrodes 45 and 46 are symmetric to each other with respect to a center point CP of the second principal surface 42b of the substrate 42. The base sections 81 are in substantially central positions in the longitudinal direction of the connection sections 51 and 61 in the comb electrodes 43 and 44. The extending sections 82 extend in the same direction as the longitudinal direction of the connection sections 51 and 61 in the comb electrodes 43 and 44.

As illustrated in FIG. 5, each of the back-side electrodes 45 and 46 is a laminate of a plurality of metal layers 91, 92, 93, and 94. That is, each of the base sections 81 and the extending sections 82 in the back-side electrodes 45 and 46 is the laminate of the plurality of metal layers 91, 92, 93, and 94.

Among the plurality of metal layers 91, 92, 93, and 94, the first metal layer 91, which is the lowest layer (nearer the substrate 42), is disposed substantially entirely along a groove section 42d in the second principal surface 42b of the substrate 42. In an exemplary aspect, the groove section 42d can conform to the shape of each of the back-side electrodes 45 and 46.

One example of the first metal layer 91 may be made of silver (Ag). The second metal layer 92 is disposed so as to cover all of the first metal layer 91. One example of the second metal layer 92 may be a nickel (Ni) film and have a thickness of about 5.0 µm. The third metal layer 93 is disposed so as to cover all of the second metal layer 92. One example of the third metal layer 93 may be a palladium (Pd) film and have a thickness of about 0.15 µm. The fourth metal layer 94 is disposed so as to cover all of the third metal layer 93. One example of the fourth metal layer 94 may be a gold (Au) film and have a thickness of about 0.07 µm. It is noted that the thickness and material of each of the first metal layer 91, second metal layer 92, third metal layer 93, and fourth metal layer 94 are provided as exemplary aspects and can be changed as appropriate.

The back-side electrode 45 having the above-described configuration is electrically connected to the comb electrode 43 by a via-hole conductor C1 charged in a via hole V1 in the substrate 42. The back-side electrode 46 is electrically connected to the comb electrode 44 by a via-hole conductor C2 charged in a via hole V2 in the substrate 42. The via-hole conductors C1 and C2 may also be referred to as conductive members or via fillers charged in the via holes V1 and V2, respectively, in the substrate 42. In an exemplary aspect, the via-hole conductors C1 and C2 are made of the same kind of metal as that of the first metal layers 71 and 91. Therefore, the comb electrodes 43 and 44 and the back-side electrodes 45 and 46 can be formed by compression molding, the occurrence of unnecessary pores in the electrodes 43, 44, 45, and 46 can be suppressed, and the electrodes 43, 44, 45, and 46 can be densely formed.

As illustrated in FIG. 5, the via holes V1 and V2 are through-holes linking the first principal surface 42a and the second principal surface 42b of the substrate 42. In the following description, the positions of the via holes V1 and V2 can be read as the positions of the via-hole conductors C1 and C2. As illustrated in FIG. 3, the via holes V1 and V2 are in positions corresponding to any of the tooth sections 53 to 56 and 64 to 67 inside a region Ar1 surround by the outer tooth sections 52, 62, and 63, which are on the opposite ends in the direction in which the tooth sections 52 to 56 and 62 to 67 in the pair of the comb electrodes 43 and 44 are aligned, and the connection sections 51 and 61. In the present embodiment, the via holes V1 and V2 are disposed in the positions corresponding to a leading end portion 54a of the inner tooth section 54 in the comb electrode 43 and a leading end portion 67a of the inner tooth section 67 in the comb electrode 44. The via holes V1 and V2 are disposed in the positions corresponding to the leading end portions of the extending sections 82 in the back-side electrodes 45 and 46 described above. In the example illustrated in FIG. 3, the via holes V1 and V2 are disposed in none of the outer tooth sections 52, 62, and 63, which are on the opposite ends in the direction in which the tooth sections 52 to 56 and 62 to 67 in the pair of the comb electrodes 43 and 44 are aligned, and the connection sections 51 and 61.

As illustrated in FIG. 5, the sensor section 41 is overlaid with a protective layer 75 collectively covering all of the comb electrodes 43 and 44 on the first principal surface 42a of the substrate 42. One example of the protective layer 75 may be a polyimide layer or a layer containing polyimide and have a thickness of about 10 μm, for example.

As illustrated in FIG. 5, one example of the oscillation circuit section 101 may be a CR oscillation circuit disposed on a circuit board 102. The oscillation circuit section 101 includes electrodes 103 and 104, and the electrodes 103 and 104 and the back-side electrodes 45 and 46 are in contact with each other and are electrically connected to each other. The oscillation circuit section 101 outputs oscillation signals corresponding to electric signals from the sensor section 41. Specifically, it outputs an oscillation signal with a frequency corresponding to a capacitance value between the pair of comb electrodes 43 and 44.

As illustrated in FIGS. 1 and 2, the oscillation circuit section 101 is connected to a control circuit section 111. In an exemplary aspect, the control circuit section 111 can be arranged inside the grip section 21 and be connected to the oscillation circuit section 101 by a wire 112. The control circuit section 111 has a configuration in which a member, such as a central processing unit (CPU), is mounted on a control circuit substrate. The control circuit section 111 detects the moisture content in a measurement target from the number of pulses of an output signal from the oscillation circuit section 101. The control circuit section 111 displays the detected moisture content on the display section 22.

As illustrated in FIGS. 1 and 2, the cover 12 includes a cover member 121 having a flat bag shape and a support member 122 attached to the cover member 121. Each of the cover member 121 and the support member 122 is made of a transparent or translucent resin. The cover 12 is attached such that the cover member 121 covers the sensor section 41 on the leading end of the probe section 31. The cover member 121 is constructed to prevent the measurement target from coming into direct contact with the leading end of the probe section 31, in particular, the sensor section 41.

The operations of the present embodiment are described below.

With the measuring device 10 in the present embodiment, when the sensor section 41 is pressed against an oral cavity (e.g., tongue) being the measurement target while the grip section 21 is gripped by a user, the moisture content in the oral cavity is measured.

In the sensor section 41 in the measuring device 10, the via holes V1 and V2 are set inside the region Ar1 in the substrate 42, and the via holes V1 and V2 are filled with the via-hole conductors C1 and C2. That is, the via holes V1 and V2 are relatively nearer the center of the substrate 42.

The advantages of the present embodiment are described below.

The via-hole conductors C1 and C2, in which many interfaces of different kinds are present and on which the effect of deformation caused by an external force tends to concentrate, are arranged in positions corresponding to any of the tooth sections 53 to 56 and 64 to 67 inside the region Ar1 surrounded by the outer tooth sections 52, 62, and 63, which are on the opposite ends in the direction in which the tooth sections 52 to 56 and 62 to 67 in the pair of comb electrodes 43 and 44 are aligned, and the connection sections 51 and 61, and thus the via-hole conductors C1 and C2 are surrounded by at least the outer tooth sections 52, 62, and 63 and the connection sections 51 and 61. Therefore, in comparison with the case where the positions of the via-hole conductors C1 and C2 are set in the connection sections 51 and 61 or the case where they are set in the outer tooth sections 52, 62, and 63, an external force is more smoothly dispersed in the exemplary configuration, and the external force acting on the comb electrodes 43 and 44 is released from the via-hole conductors C1 and C2. Because the via-hole conductors C1 and C2 are arranged inside the region Ar1, the length of the extending section 82 in each of the back-side electrodes 45 and 46 is shortened, and the parasitic capacitance dependent on the length of the extending section 82 is also reduced.

Because the pair of back-side electrodes 45 and 46 are symmetric to each other with respect to a point, an external force acting on the back-side electrodes 45 and 46 through the comb electrodes 43 and 44 can be uniformly dispersed.

Because the first metal layer 71 in each of the comb electrodes 43 and 44 is embedded in the groove section 42c of the substrate 42, the portions of the comb electrodes 43 and 44 exposed from the first principal surface 42a of the substrate 42 can be thinned. Thus, the step between the comb electrodes 43 and 44 and the first principal surface 42a of the substrate 42 is small, and, therefore, the protective layer 75 covering and protecting the comb electrodes 43 and 44 can be more uniform. Because the step is small, the amount of air contained between the measurement target and the sensor section 41 can be suppressed, and variations in measurement can be suppressed. Additionally, with the small step, the impact occurring with contact with the measurement target can be reduced.

In the present example, in which the cover 12 covers the sensor section 41, if air is contained between the cover 12 and the sensor section 41, this may cause wrinkles or twists in the cover 12, and variations in measurement may tend to occur. In the present example, however, as previously described, because the step is small, the amount of air contained between the cover 12 and the sensor section 41 can be suppressed, the occurrence of wrinkles or twists in the cover 12 can be suppressed, and thus the variations in measurement can be suppressed.

Because the first metal layers 71 and 91 are embedded in the substrate 42, the degree of close contact between the electrodes 43, 44, 45, and 46 and the substrate 42 is enhanced, the interfacial peeling is suppressed, and the back-side electrodes 45 and 46 and the oscillation circuit section 101 are directly joined. Therefore, variations in the measurement value resulting from variations in the parasitic capacitance of wire (e.g., variations in the wire-to-wire distance or in the length of the wire at the time of assembling a product or at the time of measurement) occurring with the omission of the wire can be suppressed. The elimination of the parasitic capacitance of the wire leads to improvement in the sensitivity of the sensor section 41. In addition, because the sensor section 41 and the oscillation circuit section 101 can be positioned close to each other, the head section 32 can be miniaturized (e.g., thinned), which facilitates the entry into the oral cavity.

In the present embodiment, because all of the first metal layer 71 is embedded in the groove section 42c of the substrate 42, the above-described advantages can be more noticeably obtained.

Because the via holes V1 and V2 are set immediately below the first metal layers 71 in the comb electrodes 43 and 44, the penetration of moisture, such as saliva, into the via holes V1 and V2 is suppressed, and thus the interfacial peeling at the interfaces between the via-hole conductors C1 and C2 in the via holes V1 and V2 and the substrate 42 or other areas is also suppressed.

Moreover, because the first metal layers 71 and 91 and the via-hole conductors C1 and C2 are made of the same kind of metal, the comb electrodes 43 and 44 and the back-side electrodes 45 and 46 can be formed by compression molding, the occurrence of unnecessary pores in the electrodes 43, 44, 45, and 46 can be suppressed, and they can be densely formed. Thus, the penetration of moisture into the interfaces between the first metal layers 71 and 91 and the via-hole conductors C1 and C2 is suppressed. In addition, because the via holes V1 and V2 are filled with the via-hole conductors C1 and C2, the penetration of moisture into the via holes V1 and V2 is suppressed. When the penetration of moisture into the via holes V1 and V2 is suppressed, the occurrence of a short between the back-side electrodes 45 and 46, the occurrence of a short in the circuit board 102 in the oscillation circuit section 101, a resultant decrease or loss of a function as an oral cavity moisture measuring device, and anomalous heat generation can be reduced. The elution or leakage of a metal caused by accumulated moisture (e.g., saliva) and infection occurring with the accumulation of the saliva is suppressed.

Because the via holes V1 and V2 are disposed in positions corresponding to the leading end portions of the extending sections 82 in the back-side electrodes 45 and 46, when the base sections 81 in the back-side electrodes 45 and 46 are soldered, transmission of stress on the soldered portions to the via holes V1 and V2 is reduced by the presence of the extending sections 82.

Reference Example

Next, a reference example is described. In the reference example, the same reference numerals are used for substantially the same members as those in the first embodiment, and the description of them is omitted in whole or in part.

Figure 7:
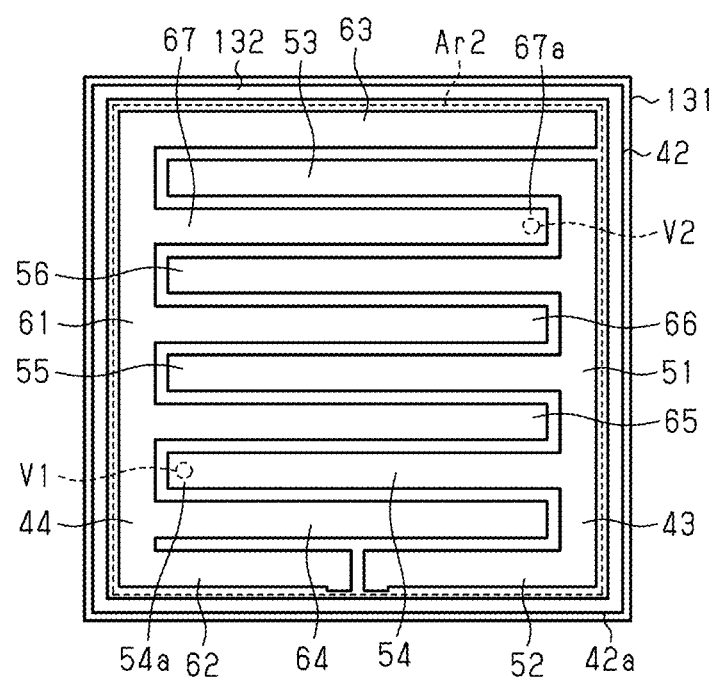
FIG. 7 is a schematic plan view of a sensor section according to a reference example.
Figure 8:
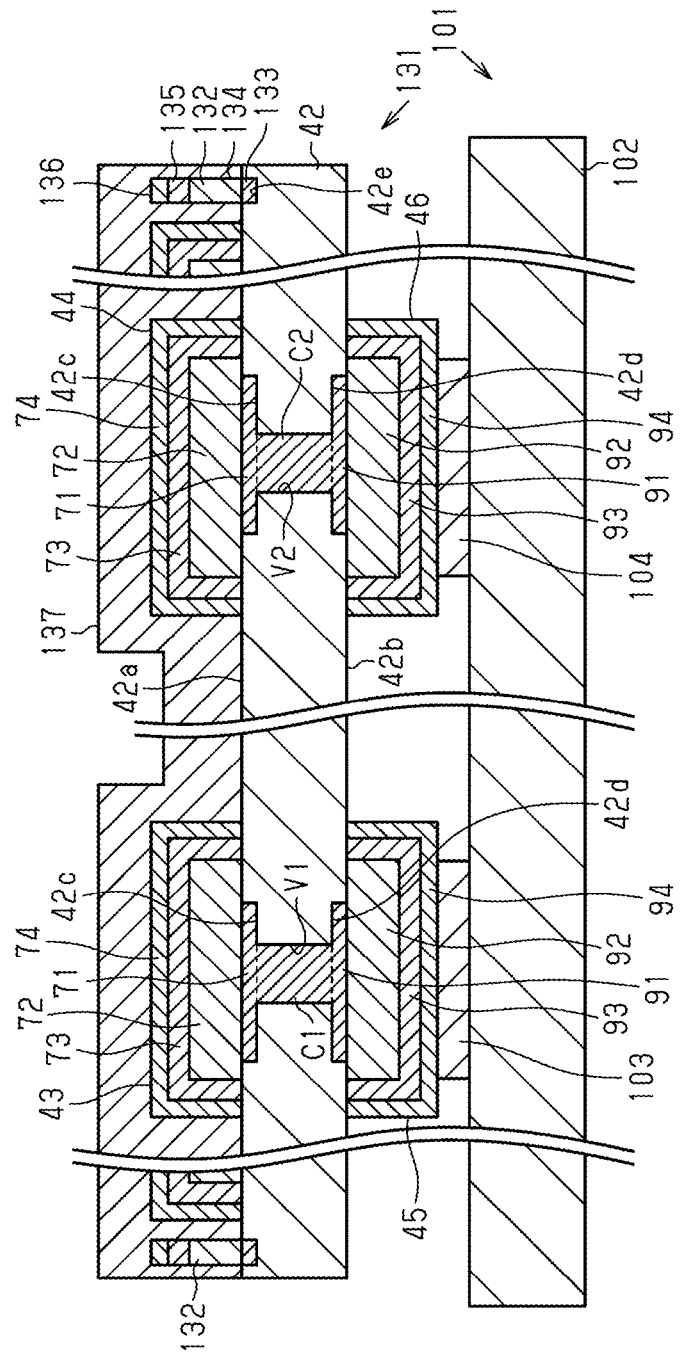
FIG. 8 is a schematic cross-sectional view of the sensor section according to the reference example.

As illustrated in FIGS. 7 and 8, the measuring device 10 according to the present reference example includes a sensor section 131 and the oscillation circuit section 101, similarly to the first embodiment.

The sensor section 131 includes the pair of comb electrodes 43 and 44 disposed on the first principal surface 42a of the substrate 42 and the back-side electrodes 45 and 46 disposed on the second principal surface 42b of the substrate 42.

The sensor section 131 includes a wall section 132 surrounding the pair of comb electrodes 43 and 44 on the first principal surface 42a of the substrate 42. The wall section 132 is a laminate of a plurality of metal layers 133, 134, 135, and 136, similarly to the comb electrodes 43 and 44. That is, the wall section 132 has the same structure as that of the pair of comb electrodes 43 and 44.

Among the plurality of metal layers 133, 134, 135, and 136, the first metal layer 133, which is the lowest layer (nearer the substrate 42), is disposed substantially entirely along a groove section 42e of the substrate 42. One example of the groove section 42e may have a rectangular frame shape conforming to the shape of the wall section 132. One example of the first metal layer 133 may be made of silver (Ag). The second metal layer 134 is disposed so as to cover all of the first metal layer 133. One example of the second metal layer 134 may be a nickel (Ni) film and have a thickness of about 5.0 μm. The third metal layer 135 is disposed so as to cover all of the second metal layer 134. One example of the third metal layer 135 may be a palladium (Pd) film and have a thickness of about 0.15 μm. The fourth metal layer 136 is disposed so as to cover all of the third metal layer 135. One example of the fourth metal layer 136 may be a gold (Au) film and have a thickness of about 0.07 μm. It is noted that the thickness and material of each of the first metal layer 133, second metal layer 134, third metal layer 135, and fourth metal layer 136 are exemplary aspects and can be changed as appropriate.

The length of the protrusion of the wall section 132 from the first principal surface 42a is substantially the same as the length of the protrusion of each of the comb electrodes 43 and 44 from the first principal surface 42a.

As illustrated in FIG. 7, the via holes V1 and V2 are through-holes linking the first principal surface 42a and the second principal surface 42b of the substrate 42. The via holes V1 and V2 are disposed in the positions corresponding to any of the tooth sections 52 to 56 and 62 to 67 inside a region Ar2 surrounded by the wall section 132. In the present reference example, similarly to the first embodiment, the via holes V1 and V2 are in the positions corresponding to the leading end portion 54a of the inner tooth section 54 in the comb electrode 43 and the leading end portion 67a of the inner tooth section 67 in the comb electrode 44. The via holes V1 and V2 are in the positions corresponding to the leading end portions of the extending sections 82 of the back-side electrodes 45 and 46 described above.

As illustrated in FIG. 8, the sensor section 131 is overlaid with a protective layer 137 collectively covering all of the comb electrodes 43 and 44 and all of the wall section 132 on the first principal surface 42a of the substrate 42. One example of the protective layer 137 may be a polyimide layer or a layer containing polyimide and have a thickness of about 10 μm.

The operations actions of the present reference example are described below.

With the measuring device 10 in the present reference example, when the sensor section 131 is pressed against an oral cavity (e.g., tongue) being a measurement target while the grip section 21 is gripped by a user, the moisture content in the oral cavity is measured.

In the sensor section 131 in the measuring device 10, the via holes V1 and V2 are set in the positions corresponding to any of the tooth sections 52 to 56 and 62 to 67 inside the region Ar2 surrounded by the wall section 132 in the substrate 42, and the via holes V1 and V2 are filled with the via-hole conductors C1 and C2. That is, the via holes V1 and V2 are relatively nearer the center of the substrate 42.

The advantages of the present reference example are described below. The present reference example can offer, in addition to the above-described advantages of the above first embodiment, the advantages described below.

Because the wall section 132 disposed on the first principal surface 42a surrounds the pair of comb electrodes 43 and 44, the wall section 132 can receive the external force acting on the comb electrodes 43 and 44, and thus the occurrence of damage to the sensor section 131 is reduced. Moreover, there may be a situation where the end portion of the sensor section 131 is pressed against an oral mucous in a less-visible oral cavity. In such a situation, because the strength of the sensor section 131 can be enhanced by the wall section 132, which is arranged in the outer area of the sensor section 131, the occurrence of damage to the sensor section 131 can be reduced.

Because the wall section 132 has the same structure as that of the pair of comb electrodes 43 and 44, the wall section 132 can be formed by the same method and at the same time as those for the comb electrodes 43 and 44. That is, in comparison with the case where the wall section is formed separately, an increase in the number of processes can be suppressed.

Because the length of the protrusion of the wall section 132 from the first principal surface 42a is substantially the same as the length of the protrusion of each of the comb electrodes 43 and 44 from the first principal surface 42a, the step in the surface of the protective layer 137 is suppressed by the wall section 132 and the comb electrodes 43 and 44.

Additional Exemplary Embodiments

The above-described embodiment and reference example can be changed and carried out as described below. It is also noted that the above-described embodiment, reference example, and variations below can be combined and carried out within the range where no technical conflict occurs.

In the above-described embodiment and reference example, the comb electrode 43 includes the five tooth sections 52 to 56, and the comb electrode 44 includes the six tooth sections 62 to 67. It should be appreciated that the numbers of the tooth sections can be changed to any numbers. For example, the number of the tooth sections in the comb electrode 43 and the number of the tooth sections in the comb electrode 44 may be the same.

In the above first embodiment, the surface of the first metal layer 71 in each of the comb electrodes 43 and 44 and the first principal surface 42a of the substrate 42 are substantially flush with each other. They are not limited thereto. For example, a configuration in which a portion of the first metal layer 71 protrudes from the first principal surface 42a of the substrate 42 and another portion of the first metal layer 71 is embedded in the substrate 42 may be adopted. A configuration in which all of the first metal layer 71 is arranged on the first principal surface 42a of the substrate 42 may also be adopted.

Figure 6:
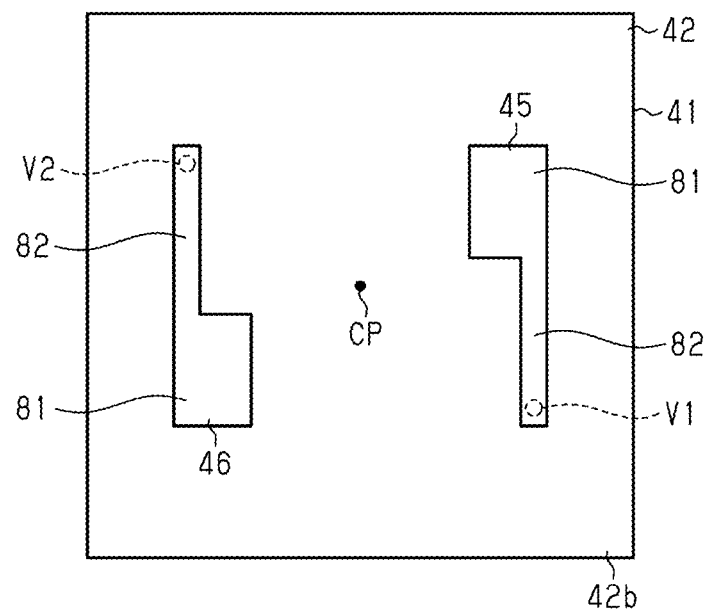
FIG. 6 is a schematic bottom view of the sensor section according to a variation of an exemplary embodiment.

In the above first embodiment, the base sections 81 are in the substantially central positions in the longitudinal direction of the connection sections 51 and 61 on the substrate 42. They are not limited thereto. As illustrated in FIG. 6, the base sections 81 may be in positions deviating from the substantially central positions in the longitudinal direction of the connection sections 51 and 61 on the substrate 42. In this manner, the positions of the base sections 81 can be changed as appropriate.

In the above reference example, the wall section 132 and the comb electrodes 43 and 44 have the same structure. Alternatively, the wall section 132 and the comb electrodes 43 and 44 may have different structures.

Unlike the above-described configuration in which the length of the protrusion of the wall section 132 from the first principal surface 42a and the length of the protrusion of the comb electrodes 43 and 44 from the first principal surface 42a are substantially the same, they may be different in alternative aspects.

In the above reference example, the configuration in which the wall section 132 is disposed on only the first principal surface 42a is adopted. However, it is noted that it is not limited thereto.

Figure 9:
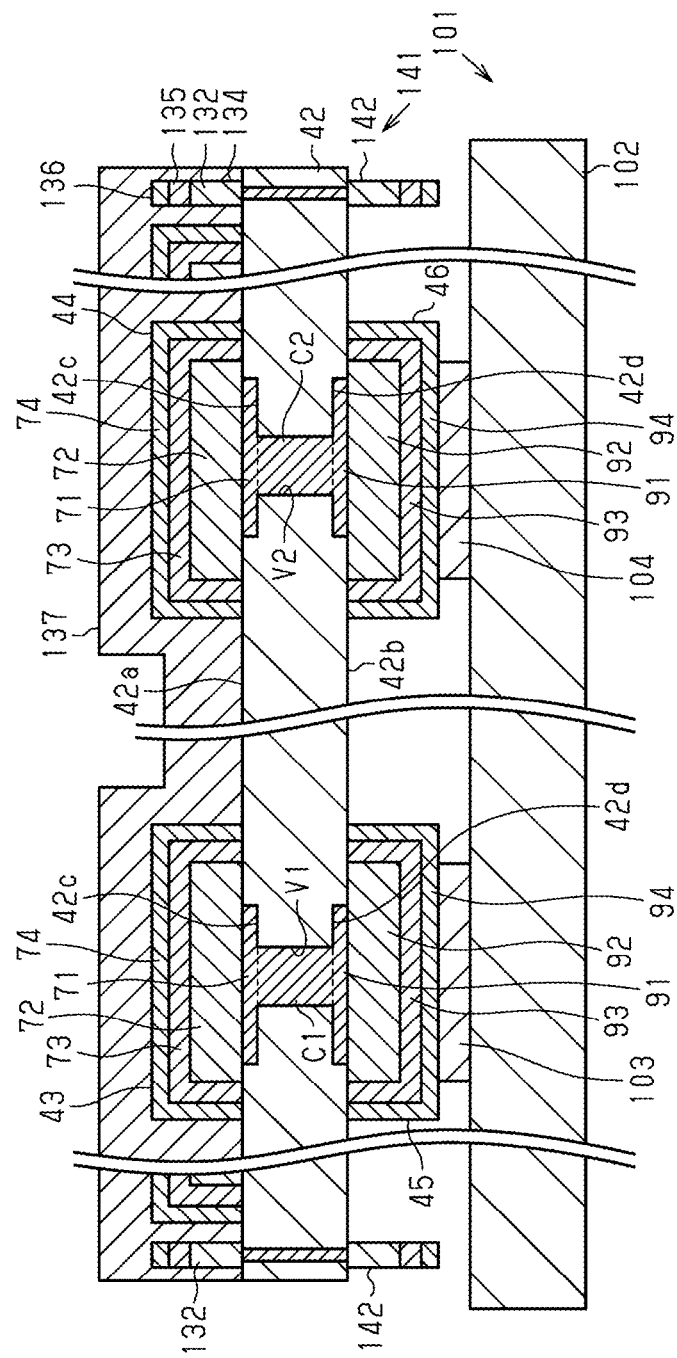
FIG. 9 is a schematic cross-sectional view of a sensor section according to a variation of an exemplary embodiment.

As illustrated in FIG. 9, a sensor section 141 can include a wall section 142 on the second principal surface 42b. The wall section 142 illustrated in FIG. 9 has the same structure as that of the wall section 132 and is positioned to oppose the wall section 132 with the substrate 42 therebetween.

Although not specifically mentioned in the above embodiment and reference example, the protective layers 75 and 137 may preferably be thinner than the substrate 42. With that configuration, the sensor section 41 can have enhanced sensitivity.

In the above-described embodiment and reference example, each of the protective layers 75 and 137 is made of polyimide. However, it is noted that the material of the protective layers 75 and 137 is not limited thereto. For example, these layers can be made of the same material as that of the substrate 42, and the protective layers 75 and 137 may have relative permittivity equal to or more than that of the substrate 42. An example of the same material as that of the substrate 42 may be a mixture of glass and ceramic material.

As described above, when the protective layer is the mixture of glass and ceramic material, the oxidation of the comb electrodes 43 and 44 can be inhibited by the protective layer covering the comb electrodes 43 and 44. Because the same material is used in the protective layer and the substrate 42, the protective layer and the substrate 42 can be tight, and the penetration of moisture from the interface between the protective layer and the substrate 42 is suppressed.

In the above-described embodiment, reference example, and variations, the configuration in which the oscillation circuit section 101 and the sensor sections 41, 131, and 141 are directly connected by direct contact between their electrodes is adopted. It is not limited thereto. For example, the configuration illustrated in FIG. 10 may be adopted.

Figure 10:
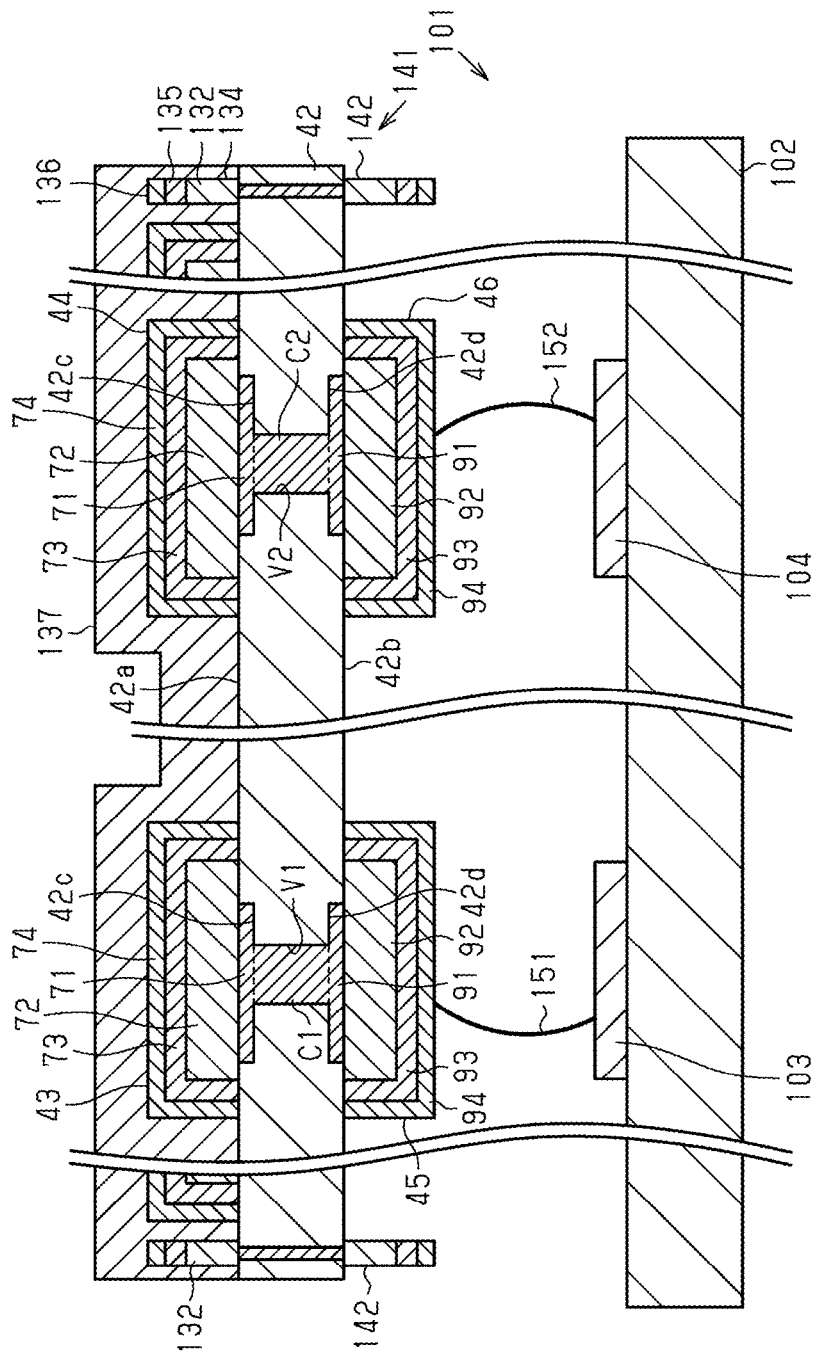
FIG. 10 is a schematic cross-sectional view of the sensor section according to a variation of an exemplary embodiment.

As illustrated in FIG. 10, the electrodes 103 and 104 in the oscillation circuit section 101 and the back-side electrodes 45 and 46 may be connected by conductors 151 and 152, which can be wires in an exemplary aspect. It is noted that the configuration illustrated in FIG. 10 is based on the variation illustrated in FIG. 9 and may also be based on the first embodiment and the reference example.

In the above-described embodiment and reference example, each of the comb electrodes 43 and 44 is the laminate of the plurality of metal layers 71, 72, 73, and 74. Each of the comb electrodes 43 and 44 may be a single metal layer (i.e., a conductive layer) as illustrated in FIG. 11.

Figure 11:
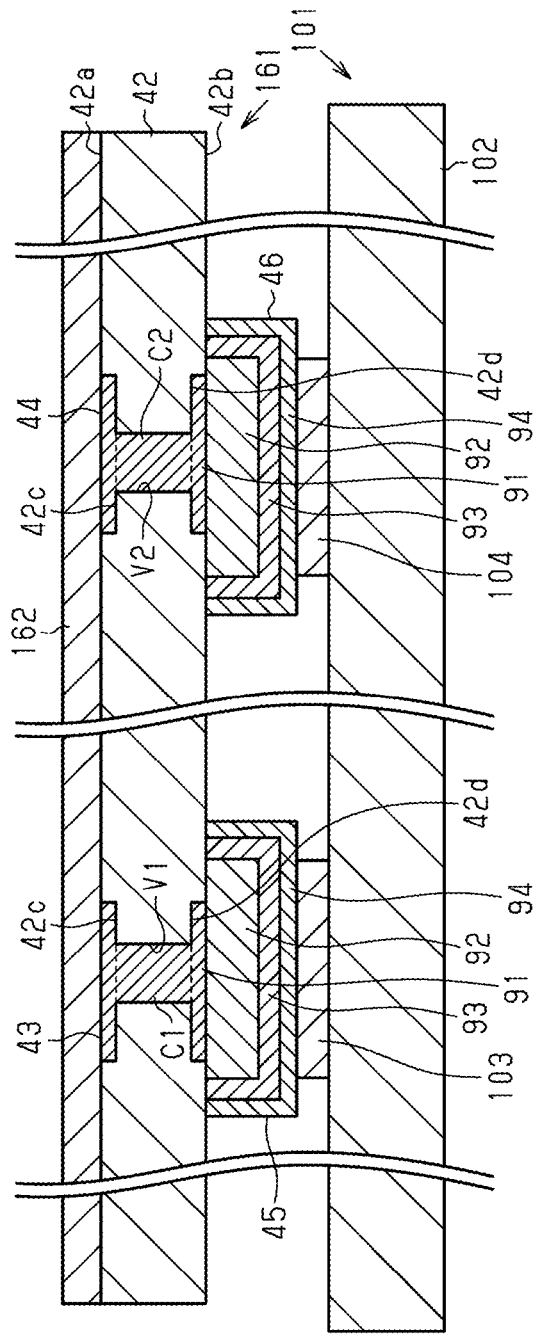
FIG. 11 is a schematic cross-sectional view of a sensor section according to a variation of an exemplary embodiment.

In the configuration of a sensor section 161 illustrated in FIG. 11, a substrate 162 covering the comb electrodes 43 and 44 is laminated. One example of the substrate 162 can preferably have relative permittivity equal to or more than that of the substrate 42.

Figure 12:
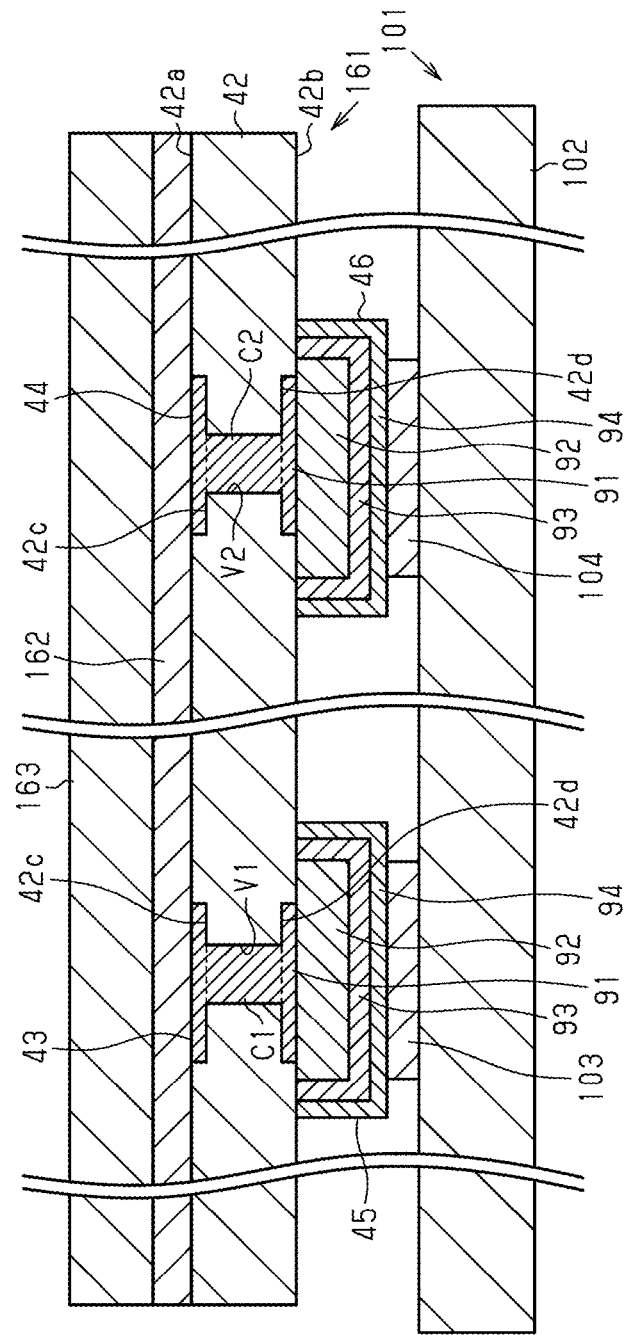
FIG. 12 is a schematic cross-sectional view of the sensor section according to a variation of an exemplary embodiment.

As illustrated in FIG. 12, the configuration in which a resin member 163 is laminated on the substrate 162 may be adopted. By covering the substrate 162 with the resin member 163, the stiffness can be increased.

The positions of the via holes V1 and V2 in the above-described embodiment and reference example are examples and can be changed inside the region Ar1 or Ar2 as appropriate. In a variation of the above reference example, the via holes V1 and V2 can be disposed immediately below the connection sections 51 and 61, for example.

Figure 13:
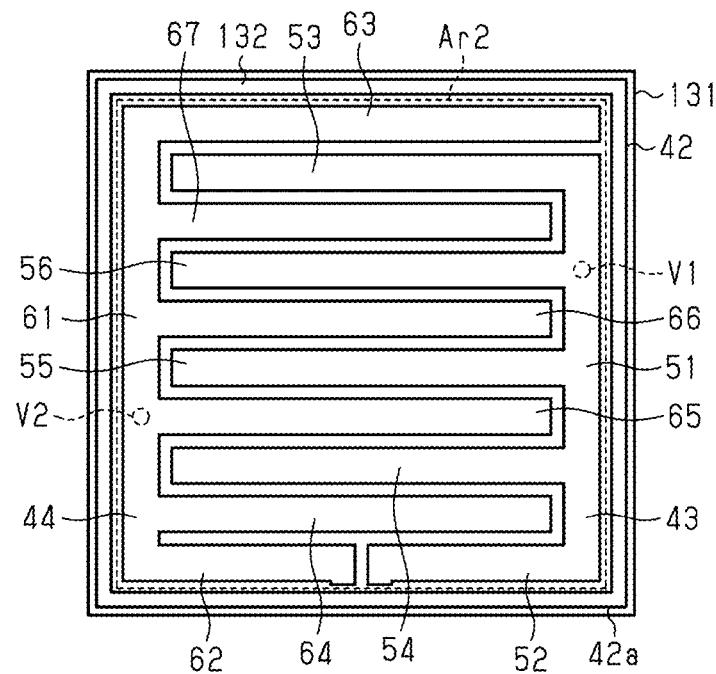
FIG. 13 is a schematic plan view of the sensor section according to a variation of an exemplary embodiment.

As illustrated in FIG. 13, the via hole V1 can be disposed immediately below a diverging point from which the tooth section 56 extends in the connection section 51, and the via hole V2 can be disposed immediately below a diverging point from which the tooth section 65 extends in the connection section 61.

Figure 14:
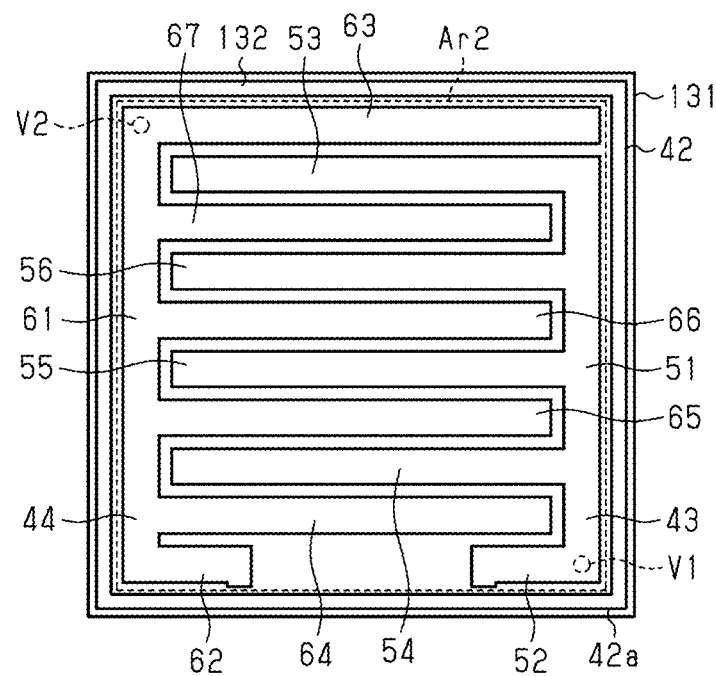
FIG. 14 is a schematic plan view of the sensor section according to a variation of an exemplary embodiment.

As illustrated in FIG. 14, the via hole V1 can be disposed immediately below a diverging point from which the outer tooth section 52 extends in the connection section 51, and the via hole V2 can be disposed immediately below a diverging point from which the outer tooth section 63 extends in the connection section 61.

As described above, when the via hole V1 is disposed immediately below the diverging point from which the tooth section extends in the connection sections 51 and 61, the stress caused by an external force acting on the comb electrodes 43 and 44 is more smoothly dispersed in the diverging direction.

Figure 15:
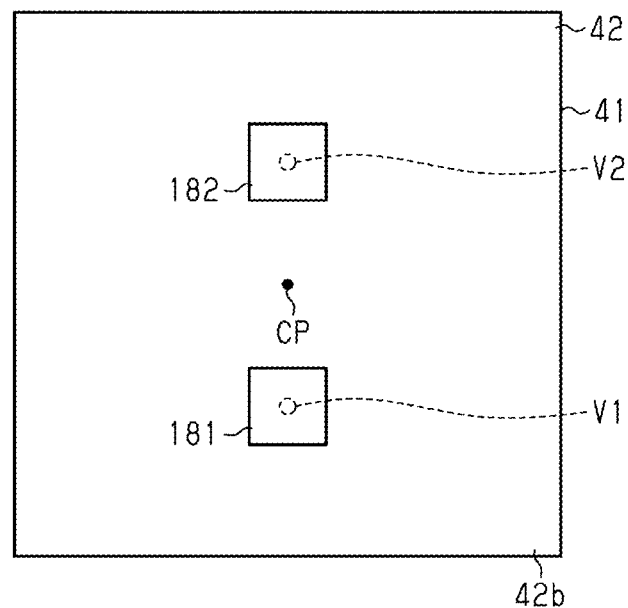
FIG. 15 is a schematic bottom view of the sensor section according to a variation of an exemplary embodiment.

In the above-described embodiment and reference example, each of the back-side electrodes 45 and 46 includes the rectangular base section 81 and the extending section 82 that extends from the base section 81. However, this configuration is not so limited thereto. For example, as illustrated in FIG. 15, a pair of back-side electrodes 181 and 182 can be rectangular. That is, the extending section 82 in each of the back-side electrodes 45 and 46 in the above-described embodiment and reference example may be omitted in this configuration. Moreover, the back-side electrodes 181 and 182 are similar to electrodes in which the base sections 81 in the back-side electrodes 45 and 46 in the above-described embodiment and reference example are rotated 90 degrees about the center point CP. Thus, the via holes V1 and V2 disposed immediately below the back-side electrodes 181 and 182 are the ones changed from them in the above-described embodiment and reference example.

Figure 16:
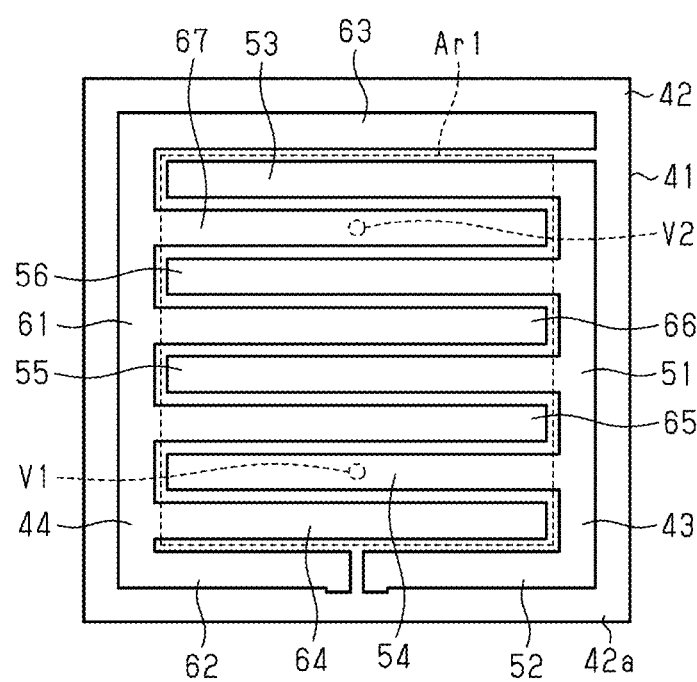
FIG. 16 is a schematic plan view of the sensor section according to the variation of an exemplary embodiment.

As illustrated in FIG. 16, the via hole V1 in the present example is disposed in a position between the ends of the tooth section 54 in the longitudinal direction (e.g., central position in the longitudinal direction). Similarly, the via hole V2 in the present example is disposed in a position between the ends of the tooth section 67 in the longitudinal direction (e.g., substantially central position in the longitudinal direction).

Figure 17:
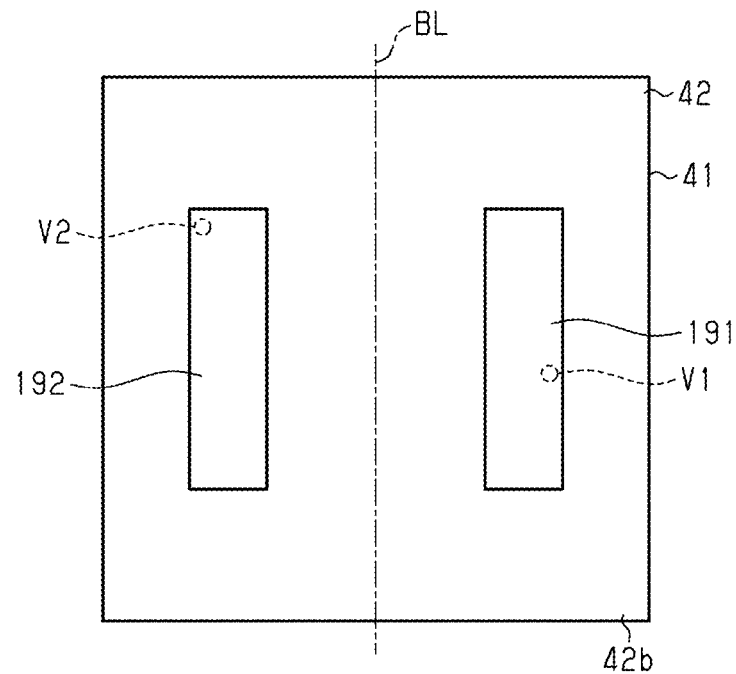
FIG. 17 is a schematic bottom view of the sensor section according to a variation of an exemplary embodiment.

In the above-described embodiment and reference example, the back-side electrodes 45 and 46 may be square, as is the case of the back-side electrodes 181 and 182 illustrated in FIG. 15, and another example of them may also be oblong, as illustrated as back-side electrodes 191 and 192 illustrated in FIG. 17, which can have a rectangular shape. As illustrated in FIG. 10, wires can be used as the conductors 151 and 152 connecting the substrate 42 and the circuit board 102. In that case, the two wires (i.e., conductors 151 and 152) connecting the back-side electrodes 45 and 46 and the oscillation circuit section 101 may preferably be routed at the same distance (i.e., with the same length) and at the same angle (e.g., in symmetrical attitudes). In this respect, when the back-side electrodes 45 and 46 are oblong, the two wires (i.e., conductors 151 and 152) connecting the back-side electrodes 45 and 46 and the oscillation circuit section 101 can be set similarly to the form in which they are at the same distance (i.e., with the same length) and at the same angle (e.g., in symmetrical attitudes) while the two via-hole conductors C1 and C2 can be spaced away from each other as much as possible, and this is useful in the improvement of design flexibility.

In the above-described embodiment and reference example, the back-side electrodes 45 and 46 are symmetric to each other with respect to the center point CP. However, this configuration is not so limited thereto.

As illustrated in FIG. 17, the back-side electrodes 191 and 192 can be symmetric to each other with respect to a reference line BL imaginarily set on the second principal surface 42*b* of the substrate 42. Here, when the rectangular substrate 42 is seen in a plan view from the direction perpendicular to the second principal surface 42*b* and when the reference line BL passing through the center of the pair of the opposite sides is set, because the back-side electrodes 191 and 192 are symmetric to each other with respect to the reference line BL as previously described, the external force acting on the back-side electrodes 191 and 192 through the comb electrodes 43 and 44 is evenly dispersed.

Figure 18:
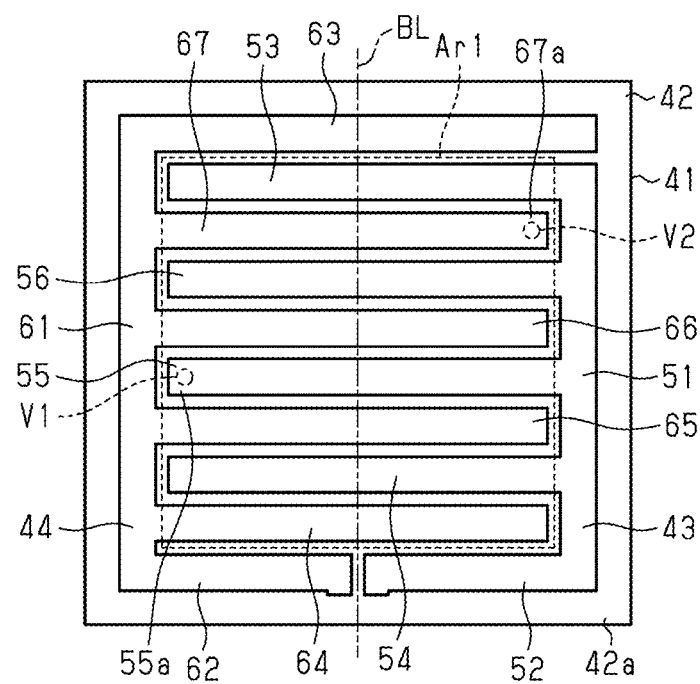
FIG. 18 is a schematic plan view of the sensor section according to the variation of an exemplary embodiment.

As illustrated in FIGS. 17 and 18, in the present example, the via hole V1 immediately below the back-side electrode 191 is in a position corresponding to a leading end portion 55*a* of the tooth section 55 in the comb electrode 43. The via hole V2 immediately below the back-side electrode 192 is in a position corresponding to the leading end portion 67*a* of the tooth section 67 in the comb electrode 44. In that case, the via holes V1 and V2 may not be in positions symmetric to each other with respect to the reference line BL.

Figure 19:
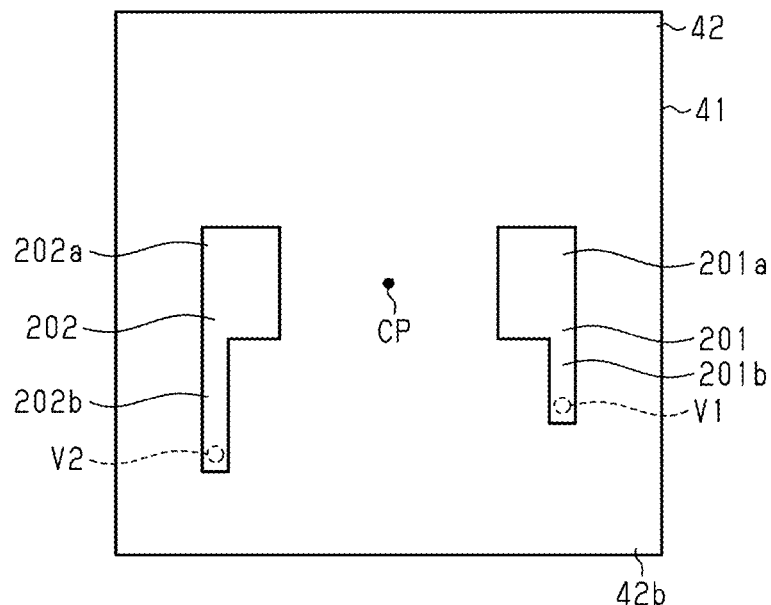
FIG. 19 is a schematic bottom view of the sensor section according to a variation of an exemplary embodiment.

As illustrated in FIG. 19, a base section 201*a* in a back-side electrode 201 and a base section 202*a* in a back-side electrode 202 may be symmetric to each other with respect to the center point CP, and an extending section 201*b* in the back-side electrode 201 and an extending section 202*b* in the back-side electrode 202 may not be symmetric to each other with respect to the point. More specifically, the length of the extension of the extending section 201*b* in the back-side electrode 201 and the length of the extension of the extending section 202*b* in the back-side electrode 202 are different. However, the extension direction of the extending section 201*b* in the back-side electrode 201 and the extension direction of the extending section 202*b* in the back-side electrode 202 are the same.

Figure 20:
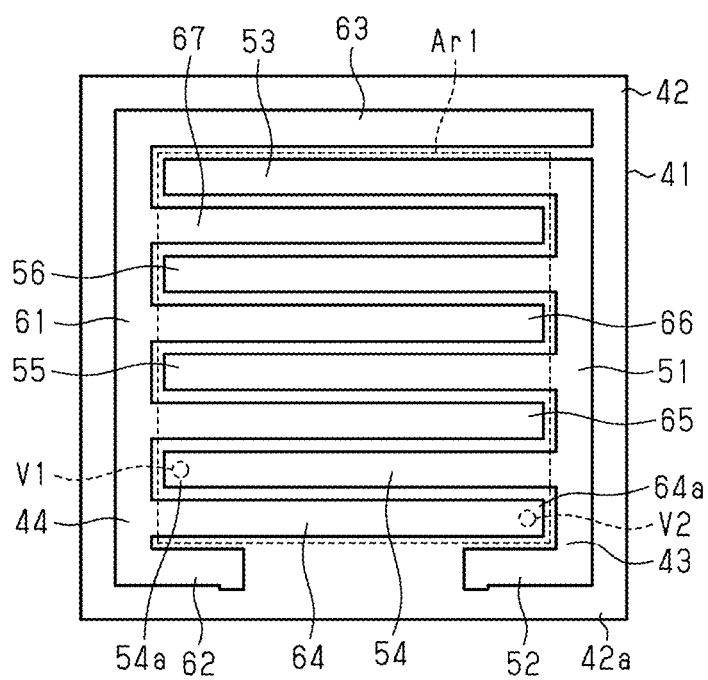
FIG. 20 is a schematic plan view of the sensor section according to the variation of an exemplary embodiment.

As illustrated in FIGS. 19 and 20, in the present example, the via hole V1 immediately below the back-side electrode 201 is in a position corresponding to the leading end portion 54*a* of the tooth section 54 in the comb electrode 43. The via hole V2 immediately below the back-side electrode 202 is in a position corresponding to a leading end portion 64*a* of the tooth section 64 in the comb electrode 44. In that case, the via holes V1 and V2 are not be in positions symmetric to each other with respect to the center point CP.

In the above-described embodiment and reference example, the distance between the tail end of the outer tooth section 52 and the tail end of the outer tooth section 62 (tail end gap) may be changed as appropriate. For example, as illustrated in FIGS. 14 and 20, the distance between the tail end of the outer tooth section 52 and the tail end of the outer tooth section 62 can be longer than that in the above-described embodiment and reference example.

In the above-described embodiment and reference example, the extension direction of the extending sections 82 in the back-side electrodes 45 and 46 extend along the longitudinal direction of the connection sections 51 and 61 in the comb electrodes 43 and 44. The extension direction of the extending sections 82 may be a direction intersecting the longitudinal direction of the connection sections 51 and 61. As one such example, a configuration in which the extension direction of the extending sections 82 extends along a direction perpendicular to the longitudinal direction of the connection sections 51 and 61 in the comb electrodes 43 and 44 (i.e., extension direction of the tooth sections 52 to 56 and 62 to 67) can be adopted.

In the above-described embodiment and reference example, the longitudinal direction of the main body 11 and the longitudinal direction of the connection sections 51 and 61 in the comb electrodes 43 and 44 are substantially the same. In addition, the longitudinal direction of the main body 11 and the longitudinal direction of the connection sections 51 and 61 in the comb electrodes 43 and 44 can intersect each other.

In the above-described embodiment and reference example, the oscillation circuit section 101 is included in the head section 32 in the probe section 31. However, it should be appreciated that the position of the oscillation circuit section 101 may be changed as appropriate. That is, a configuration in which the oscillation circuit section 101 is included in the arm section 33 in the probe section 31 or in the grip section 21 may be adopted.

In the above-described embodiment and reference example, the oscillation circuit section 101 and the control circuit section 111 are discrete elements. Alternatively, the oscillation circuit section 101 and the control circuit section 111 can be disposed on, for example, the same substrate.

Figure 21:
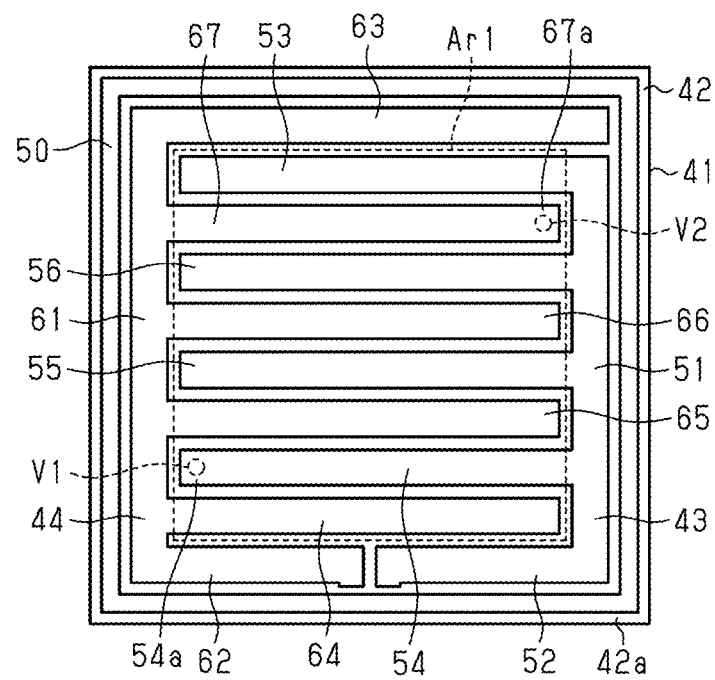
FIG. 21 is a schematic plan view of the sensor section according to a variation of the first exemplary embodiment.

As illustrated in FIG. 21, a wall section 50 protruding from the first principal surface 42a and surrounding the comb electrodes 43 and 44 can be disposed on the first principal surface 42a of the sensor section 41 in the above embodiment. In that case, because the comb electrodes 43 and 44 are surrounded by the wall section 50, the external force acting on the comb electrodes 43 and 44 can be received by the wall section 50, and the external force acting on the comb electrodes 43 and 44 can be reduced. The level of the top portion of the wall section 50 and/or the height of the protrusion of the wall section 50 from the first principal surface 42a can be set so as to reduce the external force acting on the comb electrodes 43 and 44. For example, the level of the top portion of the wall section 50 can coincide with the level of the top portion of each of the comb electrodes 43 and 44, and the height of the protrusion of the wall section 50 from the first principal surface 42a can be the same as the height of the protrusion of each of the comb electrodes 43 and 44 from the first principal surface 42a. The wall section 50 may have the same structure as that of the wall section 132 in the reference example and can be changed as described in the variations of the reference example.

In the variation illustrated in FIG. 21, the via-hole conductors C1 and C2 are disposed inside the wall section 50 and in positions corresponding to one or more tooth sections (e.g., 54 and 67) among the tooth sections 53 to 56 and 64 to 67 inside the region Ar1, which is surrounded by the outer tooth sections 52, 62, and 63, which are on the opposite ends in the direction in which the tooth sections 52 to 56 and 62 to 67 in the pair of comb electrodes 43 and 44 are aligned, and the connection sections 51 and 61. Moreover, no via-hole conductors may be disposed in the outer tooth sections 52, 62, are 63, which are on the opposite ends in the direction in which the tooth sections 52 to 56 and 62 to 67 in the pair of comb electrodes 43 and 44 are aligned, and the connection sections 51 and 61.

When the via-hole conductors C1 and C2 are arranged on the leading end portions of one or more tooth sections inside the region Ar1 (e.g., the leading end portions 54a and 67a in FIGS. 3 and 21, the leading end portions 55a and 67a in FIG. 18, the leading end portions 54a and 64a in FIG. 20), the distance between the via-hole conductors C1 and C2 can be increased, and if the stress is exerted on the via-hole conductors C1 and C2, the stress on the whole of the substrate 42 can be dispersed.

In the structure where the wall sections 132 and 142 are disposed on the first principal surface 42a and the second principal surface 42b, respectively, of the substrate 42 (e.g., in FIGS. 9 and 10), both of the wall sections 132 and 142 may possess electrical conductivity. A via-hole conductor electrically connecting the wall sections 132 and 142 may be disposed in the substrate 42. For example, in the example illustrated in FIG. 22, both of the wall sections 132 and 142 possess electrical conductivity and are electrically connected to each other by a via-hole conductor C3 disposed in the substrate 42. The wall section 142 on the second principal surface 42b is connected to a ground electrode 105 on the circuit board 102 by a conductor 153. The electrical conduction between the wall sections 132 and 142 in the sensor section 40 and the ground electrode 105 allows static electricity to the sensor section 40 from the outside environment of the sensor section 40 to be discharged to the ground electrode 105 on the circuit board 102 through the wall sections 132 and 142, and the resistance to static electricity of the sensor section 40 or of the measuring device 10 can be improved. Thus, the reliability of the measuring device 10 can be enhanced. In the example illustrated in FIG. 22, one example of the conductor 153 may be a wire.

Figure 22:
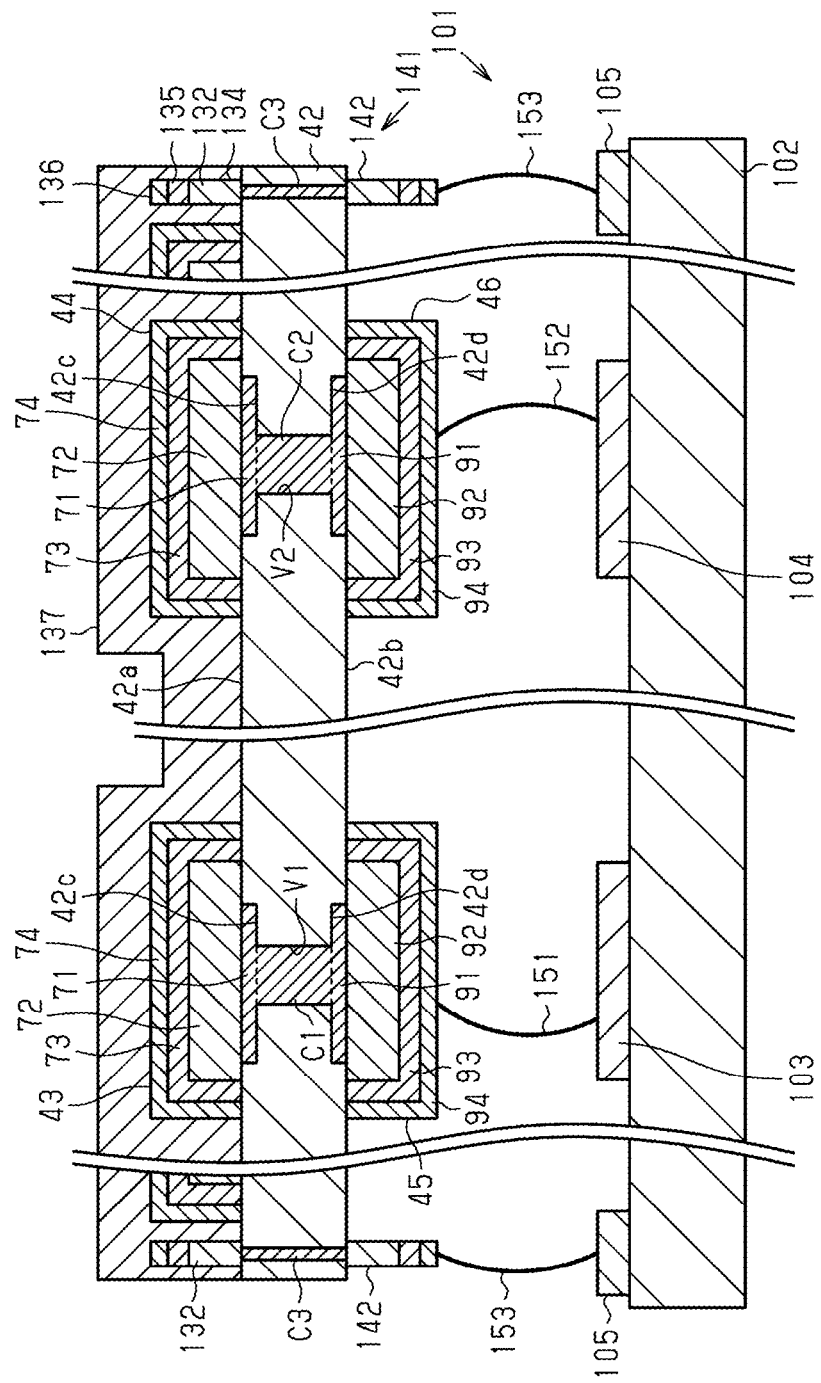
FIG. 22 is a schematic cross-sectional view of the sensor section according to a variation of the reference example.

In the example illustrated in FIG. 22, the conductors 151, 152, and 153 may be omitted, and the back-side electrodes 45 and 46 and the wall section 142 on the second principal surface 42b may be joined to the electrodes 103 and 104 and the ground electrode 105, respectively, in the oscillation circuit section 101 with solder disposed therebetween or may be connected directly to the electrodes 103 and 104 and the ground electrode 105, respectively, in the oscillation circuit section 101.

In the above-described embodiment and reference example, the measuring device for measuring the moisture content in an oral cavity is described. It can also measure the moisture content outside the oral cavity. Moreover, the cover 12 is optional, and the moisture content can be measured by pressing the sensor section 41 directly against a measurement target.

In the above-described embodiment and reference example, the measuring device measures the moisture content. It should be appreciated that it may measure other items. Examples of the measuring device may include a pH measuring device and a measuring device for measuring oral microorganisms. Another example thereof may be a measuring device for measuring a blood flow or oxygen in the blood. Another example thereof may be a measuring device for obtaining various measurement values.

The present disclosure includes configuration examples described below.

[Configuration Example 1] A measuring device includes a sensor section including a substrate having a first principal surface and a second principal surface, a pair of comb electrodes disposed on the first principal surface, and a pair of back-side electrodes disposed on the second principal surface and corresponding to the pair of comb electrodes, respectively. The sensor section further includes a wall that protrudes from the first principal surface and surrounding the pair of the comb electrodes. The substrate includes via holes in positions corresponding to tooth sections inside a region surrounded by the wall section and includes conductive members connecting the comb electrodes and the back-side electrodes disposed in the via holes.

According to Configuration Example 1, because the wall section on the first principal surface surrounds the pair of comb electrodes, the external force acting on the comb electrodes can be received by the wall section, and the occurrence of damage to the sensor section can be reduced.

[Configuration Example 2] In the measuring device described in Configuration Example 1, the wall section has the same structure as that of the pair of comb electrodes.

[Configuration Example 3] In the measuring device described in Configuration Example 1 or 2, the pair of back-side electrodes are symmetric to each other about a point.

REFERENCE SIGNS LIST

10 measuring device, 41, 131, 141, 161 sensor section, 42 substrate, 42a first principal surface, 42b second principal surface, 43, 44 comb electrode, 45, 46 back-side electrode, 51, 61 connection section, 52 to 56, 62 to 67 tooth section, 50, 132, 142 wall section, 181, 182, 191, 192, 201, 202 back-side electrode, Ar1, Ar2 region, V1, V2 via hole, C1, C2 via-hole conductor

The invention claimed is:

1. A measuring device comprising:
a sensor including a substrate having a first principal surface and a second principal surface that opposes the first principal surface, a pair of comb electrodes disposed on the first principal surface, and a pair of back-side electrodes disposed on the second principal surface,
wherein each of the pair of comb electrodes includes a connection section and plurality of tooth sections extending therefrom,
wherein the substrate includes via-hole conductors disposed in positions that correspond to the tooth sections inside a region that is surrounded by the plurality of tooth sections on opposite ends in a direction in which the plurality of tooth sections are aligned and the connection sections,
wherein the via-hole conductors connect the pair of comb electrodes and the back-side electrodes, respectively, and
wherein the connection section of each of the pair of comb electrodes extends in a first direction and the plurality of tooth sections extend in a second direction orthogonal to the first direction.

2. The measuring device according to claim 1, wherein the pair of back-side electrodes are disposed on the second principal surface at respective positions that correspond to positions of the pair of the comb electrodes of the first principal surface.

3. The measuring device according to claim 1, wherein the sensor further includes a wall that protrudes from the first principal surface and surrounds the pair of comb electrodes.

4. The measuring device according to claim 3, wherein the wall has a same structure as a structure of the pair of comb electrodes.

5. The measuring device according to claim 1, wherein the via-hole conductors are arranged on leading ends of the tooth sections inside the region.

6. The measuring device according to claim 1, wherein the pair of back-side electrodes are symmetric to each other about a central point on the second principal surface of the substrate.

7. The measuring device according to claim 1, wherein the pair of back-side electrodes comprise an oblong shape.

8. The measuring device according to claim 1, wherein each of the pair of back-side electrodes includes a base section and an extending section, and the via-hole conductors are connected to the extending sections in the pair of back-side electrodes, respectively.

9. The measuring device according to claim 1, further comprising a main body having a cuboid shape with the sensor extending from the main body.

10. The measuring device according to claim 9, wherein a longitudinal direction of the connection section of each of the pair of comb electrodes extends in a same direction as a longitudinal direction of the main body.

11. The measuring device according to claim 1, wherein a number of the plurality of tooth sections of a first comb electrode of the pair of comb electrodes is different than a number of the plurality of tooth sections of a second comb electrode of the pair of comb electrodes.

12. The measuring device according to claim 1, wherein each of the pair of comb electrodes is a laminate of a plurality of metal layers.

13. A measuring device comprising:
a sensor including a substrate having a first principal surface and a second principal surface that opposes the first principal surface, a pair of comb electrodes disposed on the first principal surface, and a pair of back-side electrodes disposed on the second principal surface,
wherein each of the pair of comb electrodes includes a connection section and plurality of tooth sections extending therefrom,
wherein the substrate includes via-hole conductors disposed in positions that correspond to the tooth sections inside a region that is surrounded by the plurality of tooth sections on opposite ends in a direction in which the plurality of tooth sections are aligned and the connection sections,
wherein the via-hole conductors connect the pair of comb electrodes and the back-side electrodes, respectively,
wherein each of the pair of comb electrodes is a laminate of a plurality of metal layers, and
wherein a first metal layer of the laminate of each of the pair of comb electrodes is embedded in a groove of the substrate of the sensor.

14. The measuring device according to claim 13, further comprising a protective layer that covers the pair of comb electrodes.

15. The measuring device according to claim 13, wherein the via-hole conductors are set immediately below the first metal layers in the pair of comb electrodes, respectively.

16. A measuring device comprising:
a sensor including a substrate having first and second surfaces that oppose each other, a pair of comb electrodes disposed on the first surface, and a pair of back-side electrodes disposed on the second surface; and
a pair of via-hole conductors extending through the substrate and that connect the pair of comb electrodes to the pair of back-side electrodes, respectively,
wherein each of the pair of comb electrodes includes a connection section and plurality of tooth sections that extend perpendicularly from the respective connection sections,
wherein the pair of via-hole conductors are disposed in the substrate and at positions inside a region that is surrounded by at least two tooth sections on opposite ends of the pair of comb electrodes, respectively, and the connection sections, and
wherein the sensor further includes a wall that protrudes from the first surface and surrounds the pair of comb electrodes.

17. The measuring device according to claim 16, wherein the pair of back-side electrodes are disposed on the second surface at respective positions that correspond to positions of the pair of the comb electrodes of the first surface.

18. The measuring device according to claim 16, wherein the via-hole conductors are arranged on leading ends of the tooth sections of the pair of comb electrodes.

* * * * *